United States Patent [19]

Cronshaw

[11] Patent Number: 4,462,248
[45] Date of Patent: Jul. 31, 1984

[54] AUTOMATIC PRESSURE/FLOW DEVICE

[75] Inventor: Arnold W. Cronshaw, Eastleigh, England

[73] Assignee: British-American Tobacco Company Limited, London, England

[21] Appl. No.: 356,172

[22] Filed: Mar. 8, 1982

[30] Foreign Application Priority Data

Mar. 18, 1981 [GB] United Kingdom ............... 8108496

[51] Int. Cl.$^3$ ............................................. G01M 3/02
[52] U.S. Cl. ..................................................... 73/38
[58] Field of Search ................................. 73/38, 37.7

[56] References Cited

U.S. PATENT DOCUMENTS

| 4,191,046 | 3/1980 | Baker et al. | 73/38 |
| 4,198,854 | 4/1980 | Washington et al. | 73/38 |
| 4,348,887 | 9/1982 | Lorenz et al. | 73/38 |

FOREIGN PATENT DOCUMENTS 2847786  5/1979  Fed. Rep. of Germany .......... 73/38

Primary Examiner—Gerald Goldberg
Assistant Examiner—Hezron E. Williams
Attorney, Agent, or Firm—Kane, Dalsimer, Kane, Sullivan and Kurucz

[57] ABSTRACT

A device for the determination of the gas permeability of a material such as paper includes a holder 1 for holding a sample across a gas flow passage of predetermined cross section and a pump 2 for drawing air through the passageway via one or more constant flow device $C_1$-$C_6$ arranged in parallel. Each constant flow device has a closable control valve $V_1$-$V_6$ respectively. A first pressure transducer measures the pressure drop across the sample and a second pressure transducer, in cooperation with a lamina flow element measures the rate of air flow through the sample. A by-pass by-passes selectively three of the control valves of the constant flow devices. The by-pass has valves $B_1$-$B_3$ arranged in parallel and operable to close the by-pass to gas flow therethrough to the respective constant flow devices $C_1$-$C_6$.

The by-pass also includes an atmospheric bleed 11 and a valve $B_4$ closable to stop the flow of air into the by-pass.

8 Claims, 1 Drawing Figure

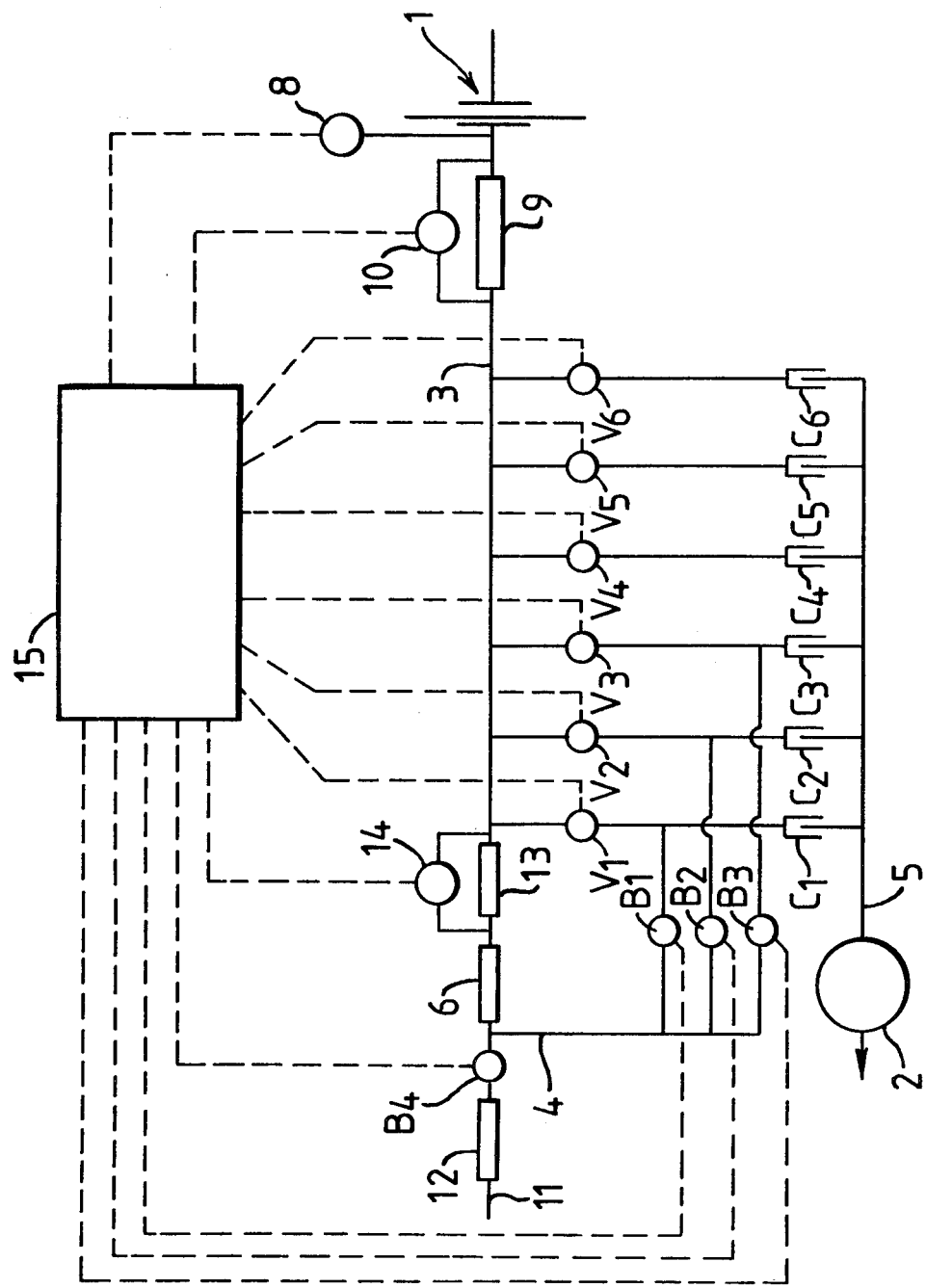

AUTOMATIC PRESSURE/FLOW DEVICE

The present invention relates to devices for the determination of the gas flow-pressure drop characteristics of gas permeable materials.

In United Kingdom Patent Specification No. 2,001,444A there is described and illustrated a device for measuring the permeability of gas permeable materials, such as paper. The device comprises a clamping head in which may be clamped a paper sample such that the sample extends transversely across an air flow passageway of predetemined cross-section. The device further comprises means for providing to the passageway a flow of air under pressure, the path of the air flow to the clamping head being through one of three flow meters. Close to the clamping head there is disposed a pressure meter operable to measure the pressure differential across the paper sample. In use of this known device the air flow is adjusted until the indicated pressure differential is at a predetermined standard value, 10 cm/WG for example, the flow meter being selected to provide a range encompassing the flow rate corresponding to the pressure differential.

There is disclosed in United Kingdom Patent Specification No. 2,018,436 a device for measuring the porosity of sheet material, such as paper. The device comprises a sample clamping head and means for establishing a gas flow transversely through the sample held in the head. The gas flows to the clamping head via a linear flow device across which is connected a pressure transducer. Control means of the device, taking the form of a microprocessor, is operable to control gas flow means of the device to set the pressure differential across the sample at a number of values close to a reference value and at each such close value to measure the corresponding flow rate, or to set the flow rate at a number of values close to a reference flow rate and at each close flow rate value to measure the corresponding pressure differential across the paper sample. The microprocessor then uses the pairs, three say, of pressure and flow values in a determination of the values of K and N in the relationship $F=K(P)^N$. The microprocessor then inserts into the aforementioned relationship either the reference pressure or the reference low rate and determines the corresponding flow rate or pressure.

Another device for measuring the porosity of sheet materials, such as cigarette paper, is described and illustrated in United Kingdom Patent Specification No. 2,038,002A. This device comprises a gas flow path to a sample clamping head, which path includes a series of constant flow devices connected in parallel. An electronic control and processing unit of the device is operable to receive pressure differential indicating signals from a pressure differential transducer having a pressure tapping point close to the clamping head. The control and processing unit is also operable to open any one of the constant flow devices. These devices are opened in sequence which results in the determination of the closest pressure values above and below a reference pressure value. Upon determination of these closest pressure values, the control and processing unit divides the flow rate at each of the closest pressure values by the respective pressure value to give closest values of flow rate per unit pressure differential. The control and processing unit then averages these values, multiplies the averaged value by the reference pressure and divides the result by the sample area to give a porosity value.

In the use of the device of United Kingdom Patent Specification No. 2,018,436A damage could be caused to the pressure transducer, which in order to possess requisite accuracy would be of a somewhat delicate form, if the permeability of the sample was of a low value and a high pressure within the flow path thus resulted.

The device of United Kingdom Patent Specification No. 2,038,022A is not capable of measuring flow rates and corresponding pressure differential values for materials having especially low permeabilities, since constant flow devices are not capable of operating accurately at the low flow rates which are established with samples of very low permeability.

The present invention provides a device for the determination of the gas flow-pressure drop characteristics of a gas permeable material, comprising holding means operable to hold a sample of said material transversely across the cross-section of a gas flow passageway; gas flow means operable to maintain a flow of gas through said passageway and through a sample of said material when held in said holding means; pressure indicating means operable to indicate gas pressure differential across the sample; flow rate indicating means operable to indicate the flow rate of gas through the sample; said gas flow means including a constant flow device and valve means intermediate said constant flow device and said holding means the valve means being operable to obturate gas flow to said constant flow device; and by-pass means by which the portion of said gas flow means intermediate said constant flow device and said valve means can be put into gas flow communication with that portion thereof intermediate said valve means and said holding means thereby by-passing said valve means said by-pass means comprising atmospheric bleed means and by-pass valve means operable to close said by-pass means including said atmospheric bleed means to gas flow therethrough.

By use of the present invention a more accurate determination may be made of the gas flow-pressure drop characteristics of gas permeable materials having low permeabilities.

Preferably the constant flow device is one of a plurality of constant flow devices of various flow rate values connected in parallel, in which case determination may be made of the gas flow-pressure drop characteristics of gas permeable materials having higher permeabilities. The by-pass means may be associated with only one of the constant flow devices or with more than one thereof. In the latter case, the by-pass means may include a plurality of by-pass valves connected in parallel each being connected to a respective one of said plurality of constant flow devices, said by pass valves being selectively closable. The arrangement may be such that the by-pass means may be put into communication simultaneously with a plurality of the constant flow devices.

Advantageously, the atmospheric bleed means is located in a branch fluid flow path branching off the part of the fluid flow path of the by-pass means which by-passes the valve means of said gas flow means.

In this case, the by-pass means includes a valve located in said branch fluid flow path and operable to close the atmospheric bleed means.

An embodiment of the present invention will now be described by way of example, with reference to the accompanying drawing which shows a schematic of a device for the determination of gas flow-pressure drop characteristics of a gas permeable sheet material such as cigarette paper.

The device comprises a sample clamping head 1 operable to hold a sample of cigarette paper transversely across a gas flow passageway of predetermined cross-section. The device further includes an air pump 2 operation of which causes air to be drawn through the sample held in the clamping head 1. The air flows from the clamping head 1 through a duct 3, one or more of a series of constant flow devices $C_1$–$C_6$ disposed in parallel and a further duct 5 to the pump 2. Connected in the duct 3 immediately downstream of the clamping head 1 is a pressure tapping of a pressure transducer 8 and a lamina flow element 9 across which is connected a pressure transducer 10. The element 9 and pressure transducer 10 permit accurate measurement of air flow within a range of 1–50 liters/minute.

The constant flow devices $C_1$–$C_6$ operate to limit air flow to nominal flow rates of 1,2,4,8,16 and 32 liters/minutes respectively. Associated with each is a respective solenoid valve ($V_1$ to $V_6$).

From duct 3 there extends a duct 4 which includes three valves $B_1$, $B_2$ and $B_3$ disposed in parallel. The duct 4, by opening the valve $B_1$ serves as a by-pass of valve $V_1$. Similarly if valve $B_2$ is opened valve $V_2$ is by-passed via duct 4, and if valve $B_3$ is opened valve $V_3$ is by-passed via duct 4. Fitted in the duct 4 between duct 3 and the valves $B_1$ to $B_3$ is an air flow resistance 6 of a predetermined valve which may suitably be of the order of 75 mm water gauge @ 1 liter/minute. Extending from the duct 4 at a location therein between resistance 6 and the valves $B_1$ to $B_3$ is an atmospheric bleed line 11 incorporating an air flow resistance 12, of a resistance value suitably of about 25 mm water gauge @ 1 liter/minute, and a valve $B_4$. Also fitted in the duct 4, between the connection thereof to duct 3 and the resistance 6 is a lamina flow element 13 across which is connected a pressure transducer 14. The element 13 and the pressure transducer 14 permit accurate measurement of air flows within a range of 0–2 liters/minute.

The device also includes control means in the form of a microprocessor 15 which is connected to the pressure transducers 8, 10 and 14 for the receipt therefrom of pressure indicating signals. The electrical interconnections are indicated by broken lines. The microprocessor is also operatively connected to the valves $V_1$–$V_6$ and to the valves $B_1$–$B_4$.

The microprocessor 15 is so programmed that in a determination routine there is first opened the valves $B_1$ and $B_4$, all of the valves $V_1$–$V_6$ being closed. Air flows to the pump 2 via the constant flow device $C_1$ which is rated at 1 liter/minute. A proportion of the air is drawn through the paper sample held in the clamping head 1 through duct 3, duct 4 and the open valve $B_1$, the remainder being provided via line 11. Thus as will be appreciated the flow rate through the paper is less than 1 liter/minute. Flow and pressure differential values from the transducers 14 and 8 are recorded by the microprocessor 15, which then proceeds to cause the valve $B_1$ to close and the valve $B_2$ to open, so that device $C_2$ acts to limit the total flow rate to 2 liters/minute, after which a further pair of flow and pressure differential values are recorded. Constant flow device $C_3$ is then placed in flow communication with the clamping head 1 in place of device $C_2$ by closing valve $B_2$ and opening valve $B_3$ and a further pair of values is recorded. Even though the device $C_3$ is rated at 4 liters/minute, the flow rate through the paper may be less than 1 liter/minute. From these three pairs of pressure/flow rate values there is calculated by the microprocessor 15 an estimated pressure differential value of the same material sample for the nominal flow rate value of the constant flow device $C_1$, i.e. that constant flow device having the lowest nominal flow rate value. This estimated pressure value is then compared with a preselected upper limit pressure value. If the estimated pressure value exceeds the limit value the determination routine is terminated. If, however, the limit value is not indicated to be exceeded, valves $B_3$ and $B_4$ are closed, so that all four valves $B_1$ to $B_4$ are closed, and valve $V_1$ is opened to intercommunicate the clamping head 1 and the air pump 2 via the constant flow device $C_1$. Pressure and flow rate values are then determined from the signals received by the microprocessor from the pressure transducers 8 and 10.

The microprocessor 15 is programmed for iterative opening and closing of the valves $V_1$–$V_6$ to produce a stepwise increasing series of nominal flow rates and to record pairs of pressure differential and actual flow rate values for each of the nominal flow rates. However, the microprocessor 15 will not proceed to establish a next higher nominal flow rate in the series until it has performed an estimation calculation to produce an estimate of the pressure differential corresponding to next higher nominal flow rate and determined that this does not exceed the limit value. If such an estimated pressure differential does exceed the limit value the determination routine is terminated. In this manner the pressure transducers 8, 10 and 14 are protected from being subjected to a pressure above the limit value, or substantially thereabove.

The number of pairs of pressure/flow rate values available for the estimation calculations increases as progress is made through the nominal flow rate series and thus the estimations are of increasing accuracy.

The microprocessor 15 may be operatively connected to a graphic display device (not shown) in order for there to be produced a display of the air flow-pressure drop curve for the sheet material sample.

What is claimed is:

1. A device for the determination of the gas flow-pressure drop characteristics of a gas permeable material, comprising a gas flow passageway, holding means operable to hold a sample of said material transversely across the cross section of said gas flow passageway; gas flow means operable to maintain a flow of gas through said passageway and through a sample of said material when held in said holding means; pressure indicating means operable to indicate gas pressure differential across the sample, flow rate indicating means operable to indicate the flow rate of gas through the sample; said gas flow means including a plurality of constant flow devices of various predetermined flow rate valves connected in parallel and valve means intermediate said constant flow devices and said holding means, said valve means being operable to obturate gas flow selectively through said constant flow devices; and by-pass means associated with a plurality of said constant flow devices by which a portion of said gas flow means intermediate said constant flow devices and said valve means can be put into gas flow communication with that portion thereof intermediate said valve means and said holding means thereby by-passing said valve means, said by-pass means including atmospheric bleed means, a closable valve for selectively closing said atmospheric bleed means and a plurality of by-pass valves connected in parallel, each being connected to a respective one of a plurality of constant flow devices, said by-pass valves and said closable valve being selectively closable to close selected ones of said constant flow devices and said said atmospheric bleed means to gas flow therethrough.

2. A device as claimed in claim 1 wherein the by-pass means includes a branch fluid flow path branching off the part of the fluid flow path of the by-pass means which by-passes the valve means of said gas flow means, the atmospheric bleed means being located in said branch fluid flow path.

3. A device according to claim 2 wherein the by-pass means includes a valve located in said branch fluid flow path and operable to close the atmospheric bleed means.

4. A device as claimed in claim 1 wherein the by-pass means is adapted to be put into fluid communication simultaneously with a plurality of said constant flow devices.

5. A device as claimed in claim 2 wherein the branch flow path of the by-pass means includes an air flow resistance between the atmospheric bleed means and the connection to the gas flow passageway.

6. A device as claimed in claim 5 wherein an air flow resistance is located in said by-pass means between the connection thereof to said gas flow means intermediate said valve means and said holding means and the connection of said branch flow path.

7. A device as claimed in claim 6 wherein a lamina flow element and a pressure transducer connected thereacross are provided in the by-pass means between the connection thereof to said gas flow means intermediate said valve means and said holding means and said further resistance.

8. A device as claimed in claim 5, 6 or 7 wherein each air flow resistance has a fixed predetermined value.

* * * * *